US007632841B2

(12) United States Patent
Dolitzky et al.

(10) Patent No.: US 7,632,841 B2
(45) Date of Patent: Dec. 15, 2009

(54) 2-N{5-[[4-[2-(METHYL-2-PYRIDINYLAMINO) ETHOXY] PHENYL]METHYL]-2,4-THIAZOLIDINEDIONE} BUTANEDIOIC ACID, METHODS OF PREPARATION AND COMPOSITIONS WITH ROSIGLITAZONE MALEATE

(75) Inventors: Yehudit Dolitzky, Petach Tikva (IL); Yoseph Avezov, Netanya (IL); Dina Spivak, Pardes-Hanna (IL); Minutza Leibovici, Netanya (IL); Ben-Zion Solomon, Petach Tikva (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 213 days.

(21) Appl. No.: 11/584,311

(22) Filed: Oct. 20, 2006

(65) Prior Publication Data
US 2007/0265313 A1 Nov. 15, 2007

Related U.S. Application Data

(62) Division of application No. 11/430,582, filed on May 9, 2006, now Pat. No. 7,435,741.

(51) Int. Cl.
*A61K 31/505* (2006.01)
*A61K 31/44* (2006.01)
(52) U.S. Cl. .................... 514/269.7; 514/342
(58) Field of Classification Search ................ 514/342
See application file for complete search history.

(56) References Cited

U.S. PATENT DOCUMENTS

| | | | |
|---|---|---|---|
| 4,812,570 A | 3/1989 | Meguro et al. |
| 5,741,803 A | 4/1998 | Pool et al. |
| 5,910,592 A | 6/1999 | Pool et al. |
| 5,919,782 A | 7/1999 | Lohray et al. |
| 5,925,656 A | 7/1999 | Kallam et al. |
| 5,952,356 A | 9/1999 | Ikeda et al. |
| 5,965,584 A | 10/1999 | Ikeda et al. |
| 6,080,765 A | 6/2000 | Ikeda et al. |
| 6,103,742 A | 8/2000 | Ikeda et al. |
| 6,121,294 A | 9/2000 | Ikeda et al. |
| 6,121,295 A | 9/2000 | Ikeda et al. |
| 6,133,293 A | 10/2000 | Ikeda et al. |
| 6,133,295 A | 10/2000 | Ikeda et al. |
| 6,150,383 A | 11/2000 | Ikeda et al. |
| 6,150,384 A | 11/2000 | Ikeda et al. |
| 6,156,773 A | 12/2000 | Ikeda et al. |
| 6,166,042 A | 12/2000 | Ikeda et al. |
| 6,166,043 A | 12/2000 | Ikeda et al. |
| 6,169,099 B1 | 1/2001 | Ikeda et al. |
| 6,169,100 B1 | 1/2001 | Ikeda et al. |
| 6,172,089 B1 | 1/2001 | Ikeda et al. |
| 6,174,904 B1 | 1/2001 | Ikeda et al. |
| 6,211,205 B1 | 4/2001 | Ikeda et al. |
| 6,211,206 B1 | 4/2001 | Ikeda et al. |
| 6,211,207 B1 | 4/2001 | Ikeda et al. |
| 6,214,848 B1 | 4/2001 | Ikeda et al. |
| 2002/0099081 A1 | 7/2002 | Sasse et al. |
| 2002/0115866 A1 | 8/2002 | Vyas |
| 2002/0133016 A1 | 9/2002 | Lynch et al. |
| 2002/0156106 A1 | 10/2002 | Buckingham et al. |
| 2002/0197940 A1 | 12/2002 | Catalfamo |
| 2003/0092742 A1 | 5/2003 | Giles et al. |
| 2003/0109552 A1 | 6/2003 | Buckingham et al. |
| 2003/0120078 A1 | 6/2003 | Sasse et al. |
| 2003/0125358 A1 | 7/2003 | Buckingham et al. |
| 2003/0139604 A1 | 7/2003 | Lynch et al. |
| 2003/0149054 A1 | 8/2003 | Hindley et al. |
| 2003/0162815 A1 | 8/2003 | Craig et al. |
| 2003/0171407 A1 | 9/2003 | Freese et al. |
| 2003/0216443 A1 | 11/2003 | Ikeda et al. |
| 2003/0220373 A1 | 11/2003 | Jaye et al. |
| 2004/0014790 A1 | 1/2004 | Craig et al. |
| 2004/0014791 A1 | 1/2004 | Craig et al. |
| 2004/0024027 A1 | 2/2004 | Craig et al. |
| 2004/0029926 A1 | 2/2004 | Craig et al. |
| 2004/0034066 A1 | 2/2004 | Craig et al. |
| 2004/0044043 A1 | 3/2004 | Craig et al. |
| 2004/0048899 A1 | 3/2004 | Buckingham et al. |
| 2004/0068116 A1 | 4/2004 | Craig et al. |
| 2004/0082620 A1 | 4/2004 | Craig et al. |
| 2004/0087629 A1 | 5/2004 | Buckingham et al. |
| 2004/0092555 A1 | 5/2004 | Blackler et al. |

(Continued)

FOREIGN PATENT DOCUMENTS

EP 0508740 10/1997

(Continued)

OTHER PUBLICATIONS

Avandament® and Avandia®, Physician's Desk Reference (2006), pp. 1343-1353.

(Continued)

*Primary Examiner*—Alton N Pryor
(74) *Attorney, Agent, or Firm*—John P. White; Cooper & Dunham LLP

(57) ABSTRACT

Disclosed is an isolated compound of the formula:

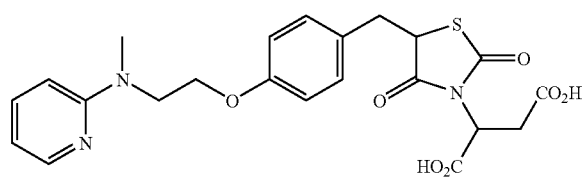

along with methods of detecting it and of minimizing it in improved pharmaceutical compositions of rosiglitazone maleate.

20 Claims, No Drawings

U.S. PATENT DOCUMENTS

| | | |
|---|---|---|
| 2004/0097556 A1 | 5/2004 | Smith |
| 2004/0102485 A1 | 5/2004 | Craig et al. |
| 2004/0106649 A1 | 6/2004 | Odaka et al. |
| 2004/0122031 A1 | 6/2004 | Hong et al. |
| 2004/0214865 A1 | 10/2004 | Sasse et al. |
| 2004/0214866 A1 | 10/2004 | Craig et al. |
| 2004/0248945 A1 | 12/2004 | Blackler et al. |
| 2004/0266833 A1 | 12/2004 | Buckingham et al. |
| 2005/0014798 A1 | 1/2005 | Turchetta et al. |
| 2005/0043539 A1 | 2/2005 | Gediya et al. |
| 2005/0112198 A1 | 5/2005 | Challapalli et al. |
| 2005/0277679 A9 | 12/2005 | Craig et al. |
| 2005/0282867 A1 | 12/2005 | Craig et al. |
| 2005/0288513 A1 | 12/2005 | Lynch et al. |
| 2006/0004058 A1 | 1/2006 | Craig et al. |
| 2006/0040993 A1 | 2/2006 | Craig et al. |
| 2007/0265312 A1* | 11/2007 | Dolitzky et al. ............. 514/342 |
| 2007/0293546 A1* | 12/2007 | Maddula et al. ............. 514/342 |

FOREIGN PATENT DOCUMENTS

| | | |
|---|---|---|
| EP | 0257781 | 9/2001 |
| WO | 9218501 | 10/1992 |
| WO | 9405659 | 3/1994 |
| WO | 9855122 | 12/1998 |
| WO | 9857634 | 12/1998 |
| WO | 9959586 | 11/1999 |

OTHER PUBLICATIONS

PCT International Preliminary Report on Patentability issued Nov. 11, 2008 in connection with PCT International Application No. PCT/US2006/017994.

* cited by examiner

2-N{5-[[4-[2-(METHYL-2-PYRIDINYLAMINO) ETHOXY] PHENYL]METHYL]-2,4-THIAZOLIDINEDIONE} BUTANEDIOIC ACID, METHODS OF PREPARATION AND COMPOSITIONS WITH ROSIGLITAZONE MALEATE

This is a divisional of U.S. Ser. No. 11/430,582, filed May 9, 2006 now U.S. Pat. No. 7,435,741, the contents of which are hereby incorporated by reference into the present application.

Throughout this application various publications, published patent applications, and patents are referenced. The disclosures of these documents in their entireties are hereby incorporated by reference into this application in order to more fully describe the state of the art to which this invention pertains.

FIELD OF THE INVENTION

The present invention relates to a rosiglitazone maleate impurity and its use as a reference marker and reference standard.

BACKGROUND OF THE INVENTION

Rosiglitazone is an oral antidiabetic agent which acts primarily by increasing insulin sensitivity. Chemically, rosiglitazone maleate is (±)-5-[[4-[2-(methyl-2-pyridinylamino) ethoxy]phenyl]methyl]-2,4-thiazolidinedione, (Z)-2-butenedioate (1:1) with a molecular weight of 473.52 (357.44 free base). The molecule has a single chiral center and is present as a racemate. Due to rapid interconversion, the enantiomers are functionally indistinguishable. (Physicians' Desk Reference (electronic version), Thomson Micromedex, Greenwood Village, Colo. (Edition expires [12/05])).

The structural formula of Rosiglitazone Maleate is:

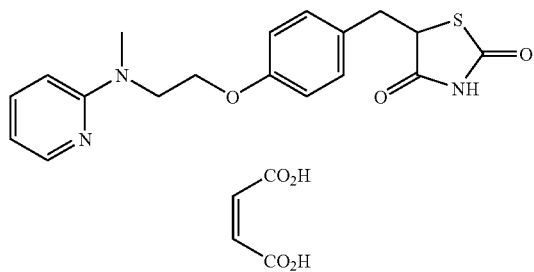

Rosiglitazone Maleate is marketed in the United States under the trade name AVANDIA® in 2 mg, 4 mg, and 8 mg tablets. In addition, Rosiglitazone Maleate in combination with Metformin HCl under the trade name AVANDAMET® in tablets with the following dosages: 1 mg/500 mg; 2 mg/500 mg; 4 mg/500 mg; 2 mg/1000 mg; 4 mg/1000 mg.

Rosiglitazone and its maleate salt are disclosed in the following United States patents, hereby incorporated by reference: U.S. Pat. Nos. 5,002,953; 5,741,803; 6,288,095.

Pharmaceutical products are regulated in most countries by governmental agencies. For example, the U.S. Food & Drug Administration (FDA) generally requires an applicant to show safety and efficacy of the pharmaceutical product during the approval/review phase and requires monitoring of the safety of the drug post-approval.

In order to satisfy safety concerns, the regulatory agencies generally require a manufacturing specification that sets the maximum amount of each identified impurity as well as the maximum amount for all remaining unidentified impurities. In addition, stability testing is performed on the pharmaceutical composition to insure that it does not substantially change over time.

Described herein is an impurity associated with rosiglitazone maleate, along with methods and formulations for minimizing the impurity.

SUMMARY OF THE INVENTION

The subject invention provides an isolated compound of the formula:

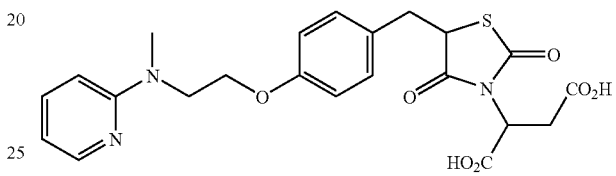

The subject invention also provides a composition comprising a compound of the formula:

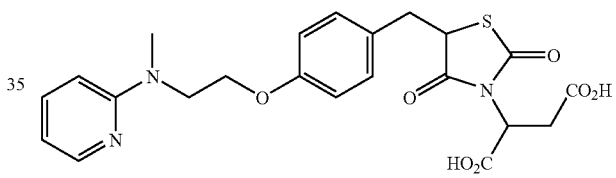

wherein the composition is free of rosiglitazone maleate.

The subject invention also provides a composition comprising a compound having the formula (I):

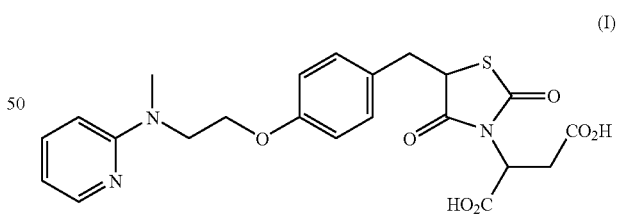

in an amount of at least 0.2% based on the weight of the composition, and a carrier.

The subject invention also provides a pharmaceutical composition comprising a granulate of a mixture of:

a) rosiglitazone maleate;

b) at least one pharmaceutically acceptable carrier; and c) less than 0.1% of the compound of the formula (I):

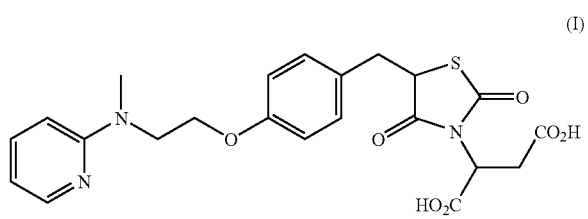

(I)

based on the combined weight of the compound of the formula (I) and rosiglitazone maleate.

The subject invention also provides a sealed package comprising:
   a pharmaceutical composition comprising rosiglitazone maleate and at least one pharmaceutically acceptable carrier; and
   a desiccant.

The subject invention also provides a process for preparing a pharmaceutical composition comprising rosiglitazone maleate and a pharmaceutically acceptable carrier, wherein the pharmaceutical composition comprises less than 1.2% of 2-N-{5-[[4-[2-(methyl-2-pyridinylamino) ethoxy]phenyl]methyl]-2,4-thiazolidinedione}-butanedioic acid, based on the combined weight of 2-N-{5-[[4-[2-(methyl-2-pyridinylamino) ethoxy]phenyl]methyl]-2,4-thiazolidinedione}-butanedioic acid and rosiglitazone maleate,
   comprising:
   a. obtaining rosiglitazone maleate drug substance;
   b. determining the total amount of 2-N-{5-[[4-[2-(methyl-2-pyridinylamino)ethoxy]phenyl]methyl]-2,4-thiazolidinedione}-butanedioic acid present in the rosiglitazone maleate drug substance; and
   c. including the rosiglitazone maleate drug substance in the preparation of the pharmaceutical composition only if the drug substance is determined to have less than 0.10% by weight of 2-N-{5-[[4-[2-(methyl-2-pyridinylamino) ethoxy]phenyl]methyl]-2,4-thiazolidinedione}-butanedioic acid.

The subject invention also provides a process for validating a batch of a pharmaceutical composition containing rosiglitazone maleate and at least one pharmaceutically acceptable carrier for distribution comprising:
   a. determining the total amount of 2-N-{5-[[4-[2-(methyl-2-pyridinylamino) ethoxy]phenyl]methyl]-2,4-thiazolidinedione}-butanedioic acid in a sample of the batch after stability testing; and
   b. validating the batch for distribution only if the sample of the batch is determined in step a) to contain less than 1.2% by weight of 2-N-{5-[[4-[2-(methyl-2-pyridinylamino) ethoxy]phenyl]methyl]-2,4-thiazolidinedione}-butanedioic acid.

DETAILED DESCRIPTION OF THE INVENTION

This invention provides an isolated compound (Compound 1) of the following structural formula:

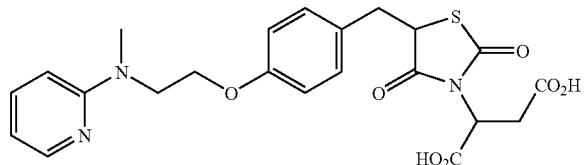

The chemical name of this compound is:
2-N-{5-[[4-[2-(methyl-2-pyridinylamino)ethoxy]phenyl]methyl]-2,4-thiazolidinedione}-butanedioic acid.

The subject invention provides a isolated compound of the formula:

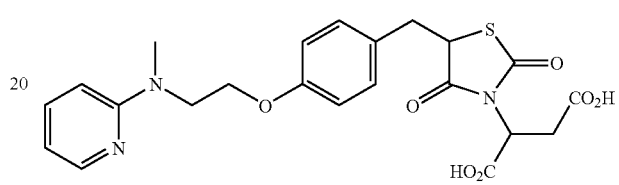

The subject invention also provides a composition comprising a compound of the formula:

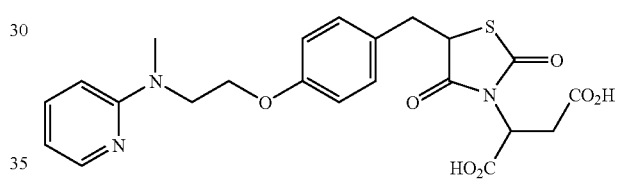

wherein the composition is free of rosiglitazone maleate.

The subject invention also provides a composition comprising a compound having the formula (I):

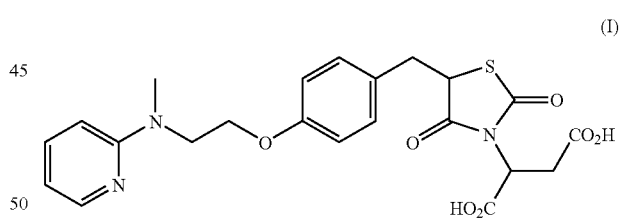

(I)

in an amount of at least 0.2% based on the weight of the composition, and a carrier.

In an embodiment, the composition comprises at least 1.5% of the compound of the formula (I), based on the weight of the composition.

In another embodiment, the composition comprises at least 50% of the compound of the formula (I), based on the weight of the composition.

In another embodiment, the composition comprises from more than 0 to 99.8% by weight of rosiglitazone maleate, based on the combined weight of the compound of the formula (I) and the rosiglitazone maleate.

In another embodiment, the composition comprises from more than 0 to 98.5% by weight of rosiglitazone maleate, based on the combined weight of the compound of the formula (I) and the rosiglitazone maleate.

In another embodiment, the composition is a pharmaceutical composition and the carrier is a pharmaceutically acceptable carrier.

In an embodiment of the pharmaceutical composition, the compound of formula (I) is present in an amount between 0.20% and 5.0% based on the combined weight of the compound of formula (I) and rosiglitazone maleate in the composition.

By 0.20% to 5.0% it is meant that all hundredth, tenth and integer unit amounts within the range are specifically disclosed as part of the invention. Thus, 0.25%, 0.30%, 0.35% . . . 4.95% unit amounts are included as embodiments of this invention.

In another embodiment of the pharmaceutical composition, the compound of formula (I) is present in an amount between 0.20% and 3.0% based on the combined weight of the compound of formula (I) and rosiglitazone maleate in the composition.

By 0.20% to 3.0% it is meant that all hundredth, tenth and integer unit amounts within the range are specifically disclosed as part of the invention. Thus, 0.25%, 0.30%, 0.35% . . . 2.95% unit amounts are included as embodiments of this invention.

In another embodiment of the pharmaceutical composition, the compound of formula (I) is present in an amount between 0.25% and 2.0% based on the combined weight of the compound of formula (I) and rosiglitazone maleate in the composition.

By 0.25% to 2.0% it is meant that all hundredth, tenth and integer unit amounts within the range are specifically disclosed as part of the invention. Thus, 0.30%, 0.35%, 0.40% . . . 1.95% unit amounts are included as embodiments of this invention.

In another embodiment of the pharmaceutical composition, the compound of formula (I) is present in an amount between 0.70% and 2.0% based on the combined weight of the compound of formula (I) and rosiglitazone maleate in the composition.

By 0.70% to 2.0% it is meant that all hundredth, tenth and integer unit amounts within the range are specifically disclosed as part of the invention. Thus, 0.75%, 0.80%, 0.85% . . . 1.95% unit amounts are included as embodiments of this invention.

In another embodiment of the pharmaceutical composition, the compound of formula (I) is present in an amount between 1.10% and 2.0% based on the combined weight of the compound of formula (I) and rosiglitazone maleate in the composition.

By 1.10% to 2.0% it is meant that all hundredth, tenth and integer unit amounts within the range are specifically disclosed as part of the invention. Thus, 1.15%, 1.20%, 1.25% . . . 1.95% unit amounts are included as embodiments of this invention.

The subject invention also provides a pharmaceutical composition comprising a granulate of a mixture of:

a) rosiglitazone maleate;

b) at least one pharmaceutically acceptable carrier; and c) less than 0.1% of the compound of the formula (I):

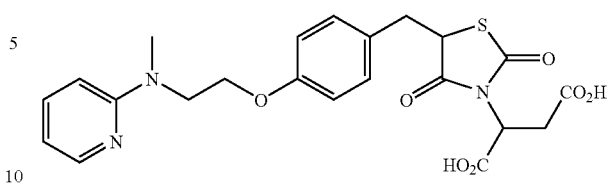

based on the combined weight of the compound of the formula (I) and rosiglitazone maleate.

In an embodiment of the pharmaceutical composition, the compound of formula (I) is present in an amount less than 0.1% based on the combined weight of the compound and rosiglitazone maleate.

In another embodiment of the pharmaceutical composition, the granulate is a product of wet granulation in an aqueous solution.

In another embodiment of the pharmaceutical composition, the granulate is a milled granulate.

In another embodiment, the pharmaceutical composition further comprises at least one disintegrant and at least one binder.

In another embodiment of the pharmaceutical composition, the disintegrant is croscarmellose sodium, and the binder is povidone.

In another embodiment, the pharmaceutical composition further comprises a biguanide antidiabetic compound.

In another embodiment of the pharmaceutical composition, the biguanide antidiabetic compound is a pharmaceutically acceptable salt of metformin.

In another embodiment of the pharmaceutical composition, the pharmaceutically acceptable salt of metformin is metformin hydrochloride.

In another embodiment, the pharmaceutical composition further comprises a sulfonyl urea antidiabetic compound.

In another embodiment of the pharmaceutical composition, the sulfonyl urea antidiabetic compound is glimepride or glipizide.

In another embodiment, the pharmaceutical composition is in the form of a tablet.

In another embodiment of the pharmaceutical composition, the tablet comprises a tablet core, the tablet core comprising, by weight, between 1% and 4% rosiglitazone maleate, 6% croscarmellose sodium, 2% povidone, between 0.5% and 1% magnesium stearate and between 87% and 90% filler, the filler consisting of lactose and microcrystalline cellulose.

In another embodiment of the pharmaceutical composition, the tablet comprises a tablet core, the tablet core comprising, by weight, between 75% and 76% metformin HCl, between 0.2% and 1% rosiglitazone maleate, between 5% and 6% povidone, between 1% and 2% croscarmellose sodium, between 4% and 5% starch, and between 0.5% and 1% magnesium stearate.

The subject invention also provides a sealed package comprising the composition described herein or the pharmaceutical composition described herein.

In an embodiment, the sealed package further comprises a desiccant.

In another embodiment of the sealed package, the desiccant is silica gel.

In another embodiment, the sealed package is a HDPE bottle.

In another embodiment of the sealed package, a net increase of the total content of a compound of the formula (I):

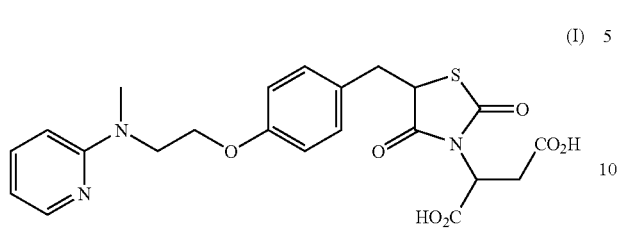

based on the combined weight of the compound of the formula (I) and rosiglitazone maleate in the pharmaceutical composition, is 0.7% or less after storage of the sealed package at 75% relative humidity and 40° C. for 3 months.

In another embodiment, the sealed package comprises the pharmaceutical composition described herein, wherein the pharmaceutical composition contains less than 1.0% of a compound of the formula (I):

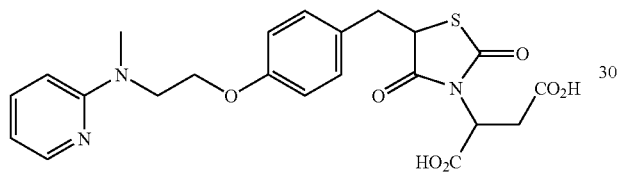

based on the combined weight of the compound of the formula (I) and rosiglitazone maleate in the pharmaceutical composition, after storage of the sealed package at 75% relative humidity and 40° C. for 3 months.

The subject invention also provides a sealed package comprising:
a pharmaceutical composition comprising rosiglitazone maleate and at least one pharmaceutically acceptable carrier; and
a desiccant.

In an embodiment of the sealed package, the pharmaceutical composition further comprises a compound of the formula (I):

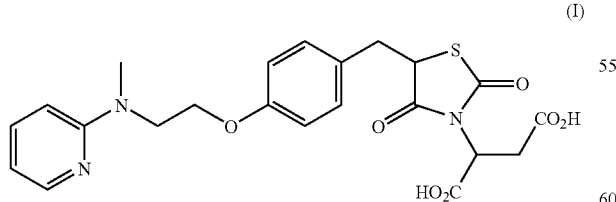

in an amount of 1.0% or below, based on the combined weight of the compound of the formula (I) and rosiglitazone maleate in the pharmaceutical composition.

In another embodiment of the sealed package, the compound of the formula (I):

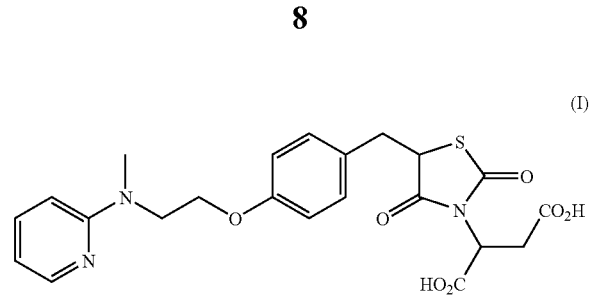

is present in the pharmaceutical composition in an amount of less than 0.1%, based on the combined weight of the compound of the formula (I) and rosiglitazone maleate.

In another embodiment of the sealed package, the pharmaceutical composition contains less than 1.0% of a compound of the formula (I):

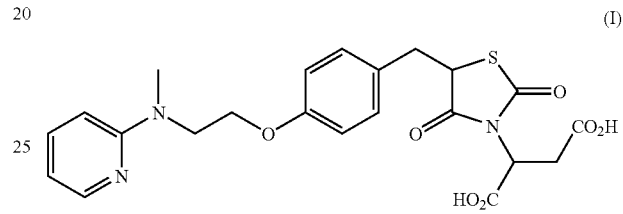

based on the combined weight of the compound of the formula (I) and rosiglitazone maleate in the pharmaceutical composition, after storage of the sealed package at 75% relative humidity and 40° C. for 3 months.

In another embodiment of the sealed package, a net increase of the total content of a compound of the formula (I):

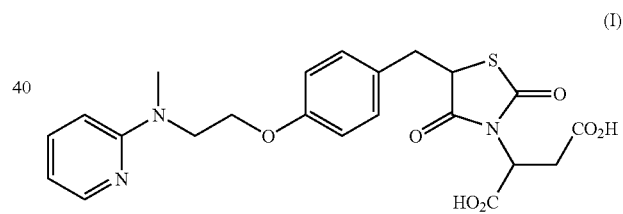

based on the combined weight of the compound of the formula (I) and rosiglitazone maleate in the pharmaceutical composition, is 0.7% or less after storage of the sealed package at 75% relative humidity and 40° C. for 3 months.

In another embodiment of the sealed package, the pharmaceutical composition further comprises at least one disintegrant and at least one binder.

In another embodiment of the sealed package, the disintegrant is croscarmellose sodium, and the binder is povidone.

In another embodiment of the sealed package, the pharmaceutical composition further comprises a biguanide antidiabetic compound.

In another embodiment of the sealed package, the biguanide antidiabetic compound is a pharmaceutically acceptable salt of metformin.

In another embodiment of the sealed package, the pharmaceutically acceptable salt of metformin is metformin HCl.

In another embodiment of the sealed package, the pharmaceutical composition further comprises a sulfonyl urea antidiabetic compound.

In another embodiment of the sealed package, the sulfonyl urea antidiabetic compound is glimepride or glipizide.

In another embodiment of the sealed package, the pharmaceutical composition is in the form of a tablet.

In another embodiment of the sealed package, the tablet comprises a tablet core, the tablet core comprising, by weight, between 1% and 4% rosiglitazone maleate, 6% croscarmellose sodium, 2% povidone, between 0.5% and 1% magnesium stearate and between 87% and 90% filler, the filler consisting of lactose and microcrystalline cellulose.

In another embodiment of the sealed package, the tablet comprises a tablet core, the tablet core comprising, by weight, between 75% and 76% metformin HCl, between 0.2% and 1% rosiglitazone maleate, between 5% and 6% povidone, between 1% and 2% croscarmellose sodium, between 4% and 5% starch, and between 0.5% and 1% magnesium stearate.

In another embodiment of the sealed package, the desiccant is silica gel.

In another embodiment of the sealed package, the pharmaceutical composition is prepared by wet granulation with water.

In another embodiment of the sealed package, the sealed package is a HDPE bottle.

The subject invention also provides a process for making the pharmaceutical composition described herein, comprising
  a) granulating in the presence of water a mixture of rosiglitazone maleate, croscarmellose sodium, povidone and a filler to obtain a granualte;
  b) drying the granulate;
  c) milling the granulate to obtain a milled granulate;
  d) mixing the milled granulate with magnesium stearate to obtain a final blend; and
  e) compressing the final blend into a tablet core.

In an embodiment of the process, steps c)-e) are performed in an atmosphere having a relative humidity of 30% or less.

The subject invention also provides another process for making the pharmaceutical composition described herein, comprising
  a) granulating in the presence of an aqueous povidone solution a mixture comprising rosiglitazone maleate and metformin to obtain a granulate;
  b) drying the granulate;
  c) milling the granulate to obtain a milled granulate;
  d) mixing the milled granulate with croscarmellose sodium and starch to obtain an first blend;
  e) mixing the first blend with magnesium stearate to obtain a final blend; and
  f) compressing the final blend into a tablet core.

In an embodiment of the process, steps c)-f) are performed in an atmosphere having a relative humidity of 30% or less.

In another embodiment, the process further comprises coating the tablet core with a film coating.

The subject invention also provides another process for preparing the pharmaceutical composition described herein or the sealed package described herein, comprising:
  a. obtaining rosiglitazone maleate drug substance;
  b. determining the total amount of 2-N-{5-[[4-[2-(methyl-2-pyridinylamino)ethoxy]phenyl]methyl]-2,4-thiazolidinedione}-butanedioic acid present in the rosiglitazone maleate drug substance; and
  c. including the rosiglitazone maleate drug substance in the preparation of the pharmaceutical composition only if the drug substance is determined to have less than 0.10% by weight of 2-N-{5-[[4-[2-(methyl-2-pyridinylamino) ethoxy]phenyl]methyl]-2,4-thiazolidinedione}-butanedioic acid.

In an embodiment of the process, the pharmaceutical composition is prepared by wet granulation in an aqueous solution.

The subject invention also provides process for preparing a pharmaceutical composition comprising rosiglitazone maleate and a pharmaceutically acceptable carrier, wherein the pharmaceutical composition comprises less than 1.2% of 2-N-{5-[[4-[2-(methyl-2-pyridinylamino)ethoxy]phenyl] methyl]-2,4-thiazolidinedione}-butanedioic acid, based on the combined weight of 2-N-{5-[[4-[2-(methyl-2-pyridinylamino) ethoxy]phenyl]methyl]-2,4-thiazolidinedione}-butanedioic acid and rosiglitazone maleate,
  comprising:
    a. obtaining rosiglitazone maleate drug substance;
    b. determining the total amount of 2-N-(5-[[4-[2-(methyl-2-pyridinylamino)ethoxy]phenyl]methyl]-2,4-thiazolidinedione)-butanedioic acid present in the rosiglitazone maleate drug substance; and
    c. including the rosiglitazone maleate drug substance in the preparation of the pharmaceutical composition only if the drug substance is determined to have less than 0.10% by weight of 2-N-{5-[[4-[2-(methyl-2-pyridinylamino) ethoxy]phenyl]methyl]-2,4-thiazolidinedione}-butanedioic acid.

In an embodiment of the process, the pharmaceutical composition is prepared by wet granulation in an aqueous solution.

The subject invention also provides a process for validating a batch of a pharmaceutical composition containing rosiglitazone maleate and at least one pharmaceutically acceptable carrier for distribution comprising:
  a. determining the total amount of 2-N-{5-[[4-[2-(methyl-2-pyridinylamino) ethoxy]phenyl]methyl]-2,4-thiazolidinedione}-butanedioic acid in a sample of the batch after stability testing; and
  b. validating the batch for distribution only if the sample of the batch is determined in step a) to contain less than 1.2% by weight of 2-N-{5-[[4-[2-(methyl-2-pyridinylamino) ethoxy]phenyl]methyl]-2,4-thiazolidinedione}-butanedioic acid.

In an embodiment of the process, the batch is validated for distribution only if the sample of the batch is determined in step a) to contain less than 1.0% by weight of 2-N-{5-[[4-[2-(methyl-2-pyridinylamino) ethoxy]phenyl]methyl]-2,4-thiazolidinedione}-butanedioic acid.

In another embodiment of the process, the batch is validated for distribution only if the sample of the batch is determined in step a) to contain less than 0.5% by weight of 2-N-{5-[[4-[2-(methyl-2-pyridinylamino)ethoxy]phenyl] methyl]-2,4-thiazolidinedione}-butanedioic acid.

The subject invention also provides a process for making the isolated compound described herein, comprising:
  a. contacting rosiglitazone maleate with water at a temperature of 40-100° C., and
  b. isolating the compound from the reaction mixture of step a).

In an embodiment of the method, the compound is isolated from the mixture via chromatography.

In another embodiment of the method, the compound is isolated from the mixture via recrystallization.

The subject invention also provides a method for increasing insulin sensitivity in a human subject comprising administering to the human subject the pharmaceutical composition described herein.

The subject invention also provides use of the composition described herein or the pharmaceutical composition described herein for manufacturing a medicament for increasing insulin sensitivity in a human subject.

The subject invention also provides a the pharmaceutical composition described herein for increasing insulin sensitivity in a human subject.

One of the methods for determining the level of Compound 1 in rosiglitazone maleate drug substance:

(a) Measuring by HPLC the area under a peak corresponding to rosiglitazone in a reference standard at a known level;

(b) Measuring by HPLC the area under a peak corresponding to Compound 1 in a sample comprising rosiglitazone maleate and Compound 1;

(c) Determining the amount of Compound 1 in the sample by comparing the area of Step (a) to the area of Step (b) and taking into account the relative response factor between Compound 1 and rosiglitazone.

As used herein, "drug substance" or "DS" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" or "DP" refers to the finished dosage form containing the drug substance as well as at least one pharmaceutically acceptable carrier.

As used herein, a "sealed" package, container or coating substantially prevents the atmosphere from coming in contact with the contents of the package or container or with the material coated by the coating.

As used herein, a "HDPE" bottle refers to a bottle constructed of high density polyethylene plastic.

Impurities can be present in the active pharmaceutical ingredient (API) or in the pharmaceutical dosage form, for example, in tablets. In the case of impurities found in the pharmaceutical dosage form and not in the corresponding API, it is possible that the excipients in the dosage form cause the degradation of rosiglitazone maleate and thereby bring about the presence of impurities. It is possible that these impurities only come into being after time and are found as a result of long term or accelerated stability studies.

Generally, side products, by-products, and adjunct reagents (collectively "impurities") are defined spectroscopically and or with another physical method, and then associated with a peak position, such as that in a chromatogram or a spot on a TLC plate. (Strobel, H. A.; Heineman, W. R., Chemical Instrumentation: A systematic Approach, $3^{rd}$ ed. (Wiley & Sons: New York 1989) p. 953.) Thereafter, the impurity can be identified by its position in the chromatogram where the position in a chromatogram is conventionally measured in minutes between injection of the sample on the column and elution of the particular component through the detector.

The retention time can vary based upon the condition of the instrumentation, as well as many other factors. To mitigate the effects such variations have upon accurate identification of an impurity, practitioners use the "Relative retention time," (RRT) to identify impurities. (Strobel p. 922) The RRT of an impurity is defined as the retention time of the impurity divided by the retention time of a reference marker. It may be advantageous to select a compound other than the API that is added to the mixture in an amount sufficiently large to be detectable and sufficiently low as not to saturate the column and to use that compound as the reference marker for determination of the RRT.

A reference standard is a compound in a relatively pure state, used to quantify the amount of the compound in an unknown mixture. A reference standard can be used as either an external standard or as an internal standard.

An external standard is employed when a solution of a known concentration of the reference standard and an unknown mixture are analyzed using the same technique. The amount of the compound in the mixture can be determined by comparing the magnitude of the detector responses.

An internal standard is employed when an unknown mixture contains a detectable amount of the reference standard compound without addition of the reference standard. The amount of internal standard is determined by preparing at least two samples by adding known and differing amounts of the internal standard. The proportion of the detector response due to the reference standard present in the mixture can be determined by plotting the detector response attained for each of the samples against the amount of the reference standard added to each of the samples and extrapolating the plot to zero.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

Specific examples of pharmaceutical acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

EXPERIMENTAL DETAILS

Example 1

Isolation of Compound 1 by Preparative HPLC 1 g of rosiglitazone maleate was mixed with 1 g of water in a reaction vessel with screw cap. The mixture was kept at 70° C. for 5 days. To this mixture, 24 mL of methanol: water solution of trifluoroacetic acid (with a pH of about 2.8) (3:2) were added. The rosiglitazone base concentration of the solution was 40 mg/mL.

Preparative HPLC was performed to the solution using the following conditions:

Column & Packing: Semi-preparative, Luna 5μ C18(2). 250× 10 mm.
Column Temperature: Ambient
Mobile Phase: Solution A—100% Water. Solution B—50:50 Water:Acetonitrile.
Elution proceeded according to the following schedule:

| Time (min) | % Solution A | % Solution B |
|---|---|---|
| 0 | 75 | 25 |
| 20 | 50 | 50 |
| 45 | 0 | 100 |
| 48 | 0 | 100 |
| 50 | 75 | 25 |
| 52 | 75 | 25 |

Flow Rate: 7.0 mL/min
Detector: DV at 245 nm, 10 mm flow cell path length
Injection Volume: 200 μL
Injector Wash Solution: Solution B.

The peaks of interest eluted at approximately 33 minutes. Separated fractions of Compound 1 were analyzed by HPLC. The relevant fractions were concentrated in vacuo using rotor evaporator and lyophilized. The obtained yield was about 8 mg. The obtained compound was determined to be Compound 1.

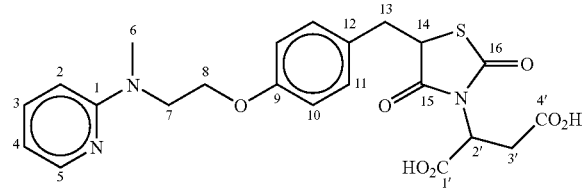

The compound was analyzed using NMR and the following spectra were attained:

| Atom # | $^1$H | $^{13}$C |
|---|---|---|
| 1 | — | 157.89 |
| 2 | 6.66 | 105.89 |
| 3 | 7.51 | 137.45 |
| 4 | 6.57 | 111.52 |
| 5 | 8.08 | 147.26 |
| 6 | 3.07 | 37.03 |
| 7 | 3.90 | 48.52 |
| 8 | 4.11 | 65.33 |
| 9 | — | 157.56 |
| 10 | 6.87 | 114.39 |
| 11 | 7.15 | 130.29 |
| 12 | — | 128.27 |
| 13 | 3.39, 3.00 | 36.55 |
| 14 | 4.99 | 50.66 |
| 15 | — | 173.22 |
| 16 | — | 170.37 |
| NH | — | — |
| 1' | — | 171.20 |
| 2' | 5.09 | 50.66 |
| 3' | 3.05, 2.65 | 33.02 |
| 4' | — | 168.98 |

MH+ MS=473 mass units. This data and the NMR analysis confirmed that Compound 1 was attained.

Example 2

Isolation of Compound 1 by Crystallization 1.3 g of rosiglitazone maleate was mixed with 1.3 g of water in a reaction vessel with screw cap. The mixture was kept at 70° C. for 5 days. 4 ml of methanol: water solution of trifluoroacetic acid with a pH of about 2.8 (3:2) were added to the mixture.

The sample was stored at 2-8° C. for 5 days. Crystals of rosiglitazone maleate enriched with Compound 1 precipitated spontaneously from the sample. These crystals were vacuum-filtered and washed with cold water and methanol. These crude crystals were then dissolved in hot isopropyl alcohol and cooled in an ice bath until crystals of Compound 1 appeared. The crystals were vacuum-filtered then washed with cold isopropyl alcohol, methanol and dried to yield 40 mg. Purity: about 97-98%.

Example 3

HPLC Analysis of Compound 1 Present in Rosiglitazone Maleate DS

Column & Packing: Zorbax Eclipse XDB C8, 5μ, 150×4.6 mm
Column Temperature: 30° C.
Mobile Phase: Buffer at pH 2.8 (20 mM sodium dihydrogen phosphate and 10 mM sodium pentanesulfonate solution):
acetonitrile (80/20)
Flow Rate: 1.5 mL/min
Detector: UV at 245 nm, 10 mm flow cell path length
Injection Volume: 20 μL Standard Solution Preparation:
Rosiglitazone maleate analytical standard was dissolved in diluent to make a solution with a concentration of approximately 0.2 μg/mL in terms of rosiglitazone.

Sample Preparation:

20 mg of the rosiglitazone maleate raw material was weighed into a 25 ml volumetric flask and dissolved in diluent.

The standard and samples were injected and the peak due to Compound 1 was monitored and calculated in the relevant sample. The peak which corresponded to Compound 1 was found to elute at approximately a Relative Retention Time of 0.7, when compared to the rosiglitazone maleate peak;

Example 4

HPLC Method for Determining Presence of Compound 1 in Formulation of Rosiglitazone Maleate Tablets or in Combined Formulation of Rosiglitazone Maleate and Metformin HCl Tablets Column & Packing: Zorbax Eclipse XDB C8, 5μ, 150×4.6 mm Column Temperature: 30° C.

Mobile Phase: Solution A-20 mM sodium dihydrogen phosphate and 10 mM sodium pentanesulfonate solution at pH 2.8.

Solution B—75% Solution A and 25% acetonitrile.

Elution proceeded according to the following schedule:

| Time (min) | Solution A % | Solution B % |
| --- | --- | --- |
| 0 | 50 | 50 |
| 15 | 0 | 100 |
| 22 | 0 | 100 |
| 24 | 50 | 50 |
| 28 | 50 | 50 |

Flow Rate: 1.5 mL/min

Detector: TV at 245 nm, 10 mm flow cell path length

Injection Volume: 15 μL

Standard Solution

Rosiglitazone maleate analytical standard was diluted with diluent to a concentration of 0.1 μg/mL.

Sample Solution Preparation

Tablets were dissolved and diluted based on the declared strengths.

The standard and samples were injected and the peaks due to Compound 1 were monitored and calculated in the relevant sample.

The quantifiable limit of this method was determined to be 0.1% based on the combined weight of Compound 1 and rosiglitazone.

Example 5a

Preparation of Tablets Comprising Rosiglitazone Maleate and Metformin

Tablets were prepared using the excipients in Table 1.

TABLE 1

| MATERIAL | Metformin HCl/ Rosiglitazone Maleate 500/1 & 1000/2 mg % W/W | Metformin HCl/ Rosiglitazone Maleate 500/2 & 1000/4 mg % W/W | Metformin HCl/ Rosiglitazone Maleate 500/4 mg % W/W |
| --- | --- | --- | --- |
| Part I | | | |
| Metformin HCl | 75.76 | 75.6 | 75.0 |
| Povidone USP(PVP K-30) | 3.03 | 3.03 | 3.01 |
| Part II | | | |
| Microcrystalline Cellulose NF | 2.88 | 2.87 | 2.86 |
| Colloidal Silicon Dioxide | 0.03 | 0.03 | 0.03 |
| Part III | | | |
| Rosiglitazone Maleate | 0.20 | 0.4 | 0.80 |
| Microcrystalline Cellulose NF | 2.88 | 2.87 | 2.86 |
| Part IV | | | |
| Microcrystalline Cellulose NF Granulation Solution | 0.30 | 0.30 | 0.30 |
| Povidone USP (PVP K-90) in hot purified water | 2.73 | 2.72 | 2.71 |
| Part V | | | |
| Croscarmellose Sodium NF- | 1.59 | 1.59 | 1.58 |
| Microcrystalline Cellulose NF- | 5.30 | 5.3 | 5.27 |
| Starch NF | 4.39 | 4.34 | 4.37 |
| Part VI | | | |
| Magnesium Stearate NF | 0.91 | 0.91 | 0.90 |
| Total (Cores) | 100.0 | 100.0 | 100.0 |
| Film coating (% calculated as per core weight) | 3.0 | 3.0 | 3.0 |

1. Metformin HCl & Povidone (PVP K-30) of Part I were transferred to a high shear mixer and mixed.

2. Microcrystalline cellulose and Colloidal Silicon Dioxide of part II were screened and mixed in a Y-cone mixer with Rosiglitazone and Microcrystalline cellulose of Part III and with Microcrystalline cellulose of part IV.

3. The mixture from Step 2 was transferred to the high shear mixer from Step 1 and mixed.

4. Povidone (PVP K-90) solution in hot purified water was added to the high shear mixer from Step 3 & was mixed to attain a wet granulate.

5. The granulate from Step 4 was dried in a Fluid Bed Dryer.

Steps 6 to 10 which follow were performed in an atmosphere with lower than 30% relative humidity.

6. The dried granulate was milled and transferred to a Flow bin or Y-cone.

7. Components of part V were screened through a sieve, transferred to Flow bin or Y-Cone from Step 6, and mixed.

8. Magnesium stearate was screened through a sieve, transferred to Flow bin or Y-cone from Step 7, and mixed to get the final blend.

9. The final blend from Step 8 was compressed into cores in a tableting machine to yield tablet cores of the appropriate dosages.

10. The cores were coated using OPADRY®, which consists of HPMC2910/HYPROMELLOSE 6 cP, Titanium dioxide, Macrogol/PEG 400, Iron Oxide yellow/iron oxide red; using a coating machine.

Example 5b

Preparation of Tablets Comprising Rosiglitazone Maleate

Tablets were prepared using the excipients below.

| MATERIAL | Rosiglitazone Maleate Tabs (2 mg base) % W/W | Rosiglitazone Maleate Tabs (4 mg base) % W/W | Rosiglitazone Maleate Tabs (8 mg base) % W/W |
|---|---|---|---|
| Part I | | | |
| Lactose Monohydrate NF | 45.2 | 44.33 | 44.33 |
| Croscarmellose Sodium NF | 6.0 | 6.0 | 6.0 |
| Rosiglitazone Maleate | 1.77 | 3.53 | 3.53 |
| Povidone USP (PVP K-30) | 2.0 | 2.0 | 2.0 |
| Microcrystalline Cellulose NF | 44.36 | 43.47 | 43.47 |
| Purified water USP | as needed | as needed | as needed |
| Part II | | | |
| Magnesium Stearate NF | 0.67 | 0.67 | 0.67 |
| Total (Cores) | 100.0 | 100.0 | 100.0 |
| Film coating(% calculated as per core weight) | 3.0 | 3.0 | 3.0 |

Production Method

1. The components of Part I were transferred to a high shear mixer and mixed.

2. Purified water (granulation solution) was added to the high shear mixer from Step 1 and mixed, and a wet granulate was attained.

3. The granulate from Step 2 was dried in a Fluid Bed Dryer.

Steps 4 to 7 which follow were performed in an atmosphere with lower than 30% relative humidity.

4. The dried granulate was milled and transferred to a flow bin or Y-cone and mixed.

5. Magnesium stearate was screened through a sieve, transferred to the flow bin or Y-cone from Step 4 and mixed to attain the final blend.

6. The final blend from Step 5 was compressed in to cores in a tableting machine.

7. The cores were coated in a coating machine using Opadry® which consists of: HPMC2910/HYPROMELLOSE 6 cP, Titanium dioxide, Macrogol/PEG 3350, Triacetin/Glycerol, Triacetate, Talc, Iron Oxide yellow/red/black, FD&C Blue#2/Indigo Carmine Aluminum Lake.

Example 6

Thermodegradation Study

Two batches of Rosiglitazone maleate drug substance were analyzed for presence of Compound 1 after thermodegradation, and after storage at RT, using the method described in Example 4.

Also, drug product (500 mg metformin/4 mg rosiglitazone base) prepared as in Example 5a made from two different batches of the rosiglitazone maleate drug substance was analyzed for presence of Compound 1 before and after thermodegradation using the method described in Example 4.

The thermodegradation was performed by subjecting the samples to 65° C. heat and 100% relative humidity for 5 days. The content of Compound 1 is listed in the table below. The peaks were measured and the area percent (area of Compound 1 peak/area of all rosiglitazone related peaks) of the Compound 1 peak is listed below.

| Sample | Content of Compound 1 without thermo-degradation % (w/w) | Content of Compound 1 after thermo-degradation % (w/w) |
|---|---|---|
| DS A | 0.0 | 0.03 |
| DS B | 0.16 | 0.18 |
| DP A | 0.0 | 0.68 |
| DP B | 0.15 | 1.05 |

This Example shows that Compound 1 is formed to a greater extent in DP than in the DS.

Example 7

Compatibility Study

Rosiglitazone maleate was mixed with various excipients and with metformin in the same proportions as present in the 500 mg/4 mg (base strength) metformin/rosiglitazone maleate tablets. 0.5 ml of water was added to each mixture, and the samples were kept at 65° C. for 4 days. The amount of Compound 1 was determined in each of the samples using the method in Example 4. The results are summarized in the table below. The peaks were measured and the area percent (area of Compound 1 peak/area of all rosiglitazone related peaks) of the Compound 1 peak is listed below.

| Sample | Area Percent |
|---|---|
| Rosiglitazone Maleate (alone) | 0.9 |
| PVP K90 | 1.3 |
| PVP K30 | 1.5 |
| Metformin HCl | 0.2 |
| Avicel | 2.9 |
| Croscarmellose | 0.3 |
| Starch | 6.7 |
| Mg Stearate | 0.3 |
| Placebo mix A | 0.1 |
| Placebo mix B | 0.1 |

Placebo mix A refers to a mixture of excipients as indicated in Example 5a, with the exception of rosiglitazone maleate.

Placebo mix B refers to a mixture of excipients as indicated in Example 5b, with the exception of rosiglitazone maleate.

This Example indicates that the presence of moisture and some excipients, especially starch, enhances the production of Compound 1 in accelerated conditions.

Example 8

Stability of Tablets

Tablets were prepared as described in Example 5. 100 tablets were packed into high density polyethylene (HDPE) bottles either with or without silica gel and were stored at 75% RH and 40° C. for 3 months. The tablets were then tested for Compound 1. The results, in terms of percentage of Compound 1 are listed in the table below. The percentage of compound in all of the dosages in the table below before the stability testing was less than 0.1%.

| Tablets | Stored without silica gel | Stored with silica gel |
|---|---|---|
| 500/1 mg | 0.7 | 0.4 |
| 1000/2 mg | 0.6 | 0.4 |
| 500/2 mg | 0.8 | 0.5 |
| 1000/4 mg | 1.0 | 0.5 |
| 500/4 mg | 1.3 | 0.7 |

It can be seen from this experiment that the absence of water in pharmaceutical compositions comprising rosiglitazone maleate enhances stability. Addition of silica gel to packaging of pharmaceutical compositions comprising rosiglitazone maleate reduces the formation of Compound 1.

Example 9

Measurement of Content of Compound 1 in AVANDAMET® 1000/2 mg Tablets

The amount of Compound 1 in commercially available AVANDAMET® tablets 1000/2 mg was analyzed using Example 4. Compound 1 was present in an amount that was less than quantifiable.

What is claimed:

1. A sealed package comprising a pharmaceutical composition, wherein the pharmaceutical composition comprises a compound having the formula (I)

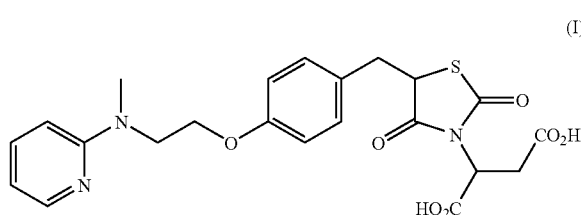

(I)

in an amount of at least 0.2% by weight, and rosiglitazone maleate in an amount from more than 0 to 99.8% by weight, the amounts based on the combined weight of the compound of the formula (I) and the rosiglitazone maleate.

2. The sealed package of claim 1, further comprising a desiccant.

3. The sealed package of claim 2, wherein the desiccant is silica gel.

4. The sealed package of claim 1, which is a high density polyethylene bottle.

5. The sealed package of claim 1, wherein a net increase of the total content of a compound of the formula (I):

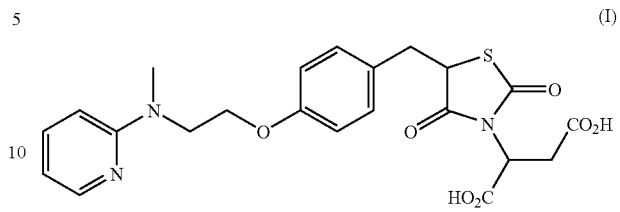

(I)

based on the combined weight of the compound of the formula (I) and rosiglitazone maleate in the pharmaceutical composition, is 0.7% or less after storage of the sealed package at 75% relative humidity and 40° C. for 3 months.

6. A sealed package comprising pharmaceutical composition wherein the pharmaceutical composition comprises a granulate of a mixture of a) rosiglitazone maleate; b) at least one pharmaceutically acceptable carrier; and c) a compound of the formula (I)

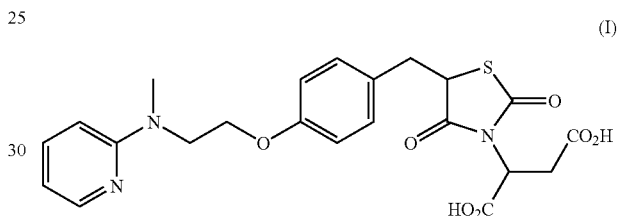

(I)

present in an amount less than 0.1% based on the combined weight of the compound of the formula (I) and rosiglitazone maleate in the pharmaceutical composition, and wherein after storage of the sealed package at 75% relative humidity and 40° C. for 3 months the pharmaceutical composition contains less than 1.0% of the compound of formula (I).

7. A sealed package comprising: a pharmaceutical composition comprising rosiglitazone maleate and at least one pharmaceutically acceptable carrier;

a compound of the formula (I):

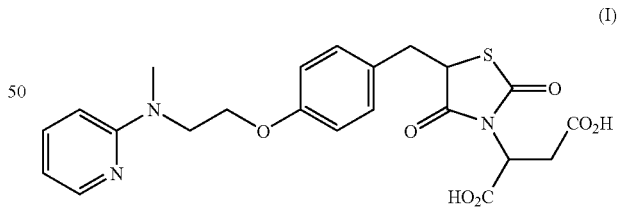

(I)

which is present in an amount of 1.0% or below, based on the combined weight of the compound of the formula (I) and rosiglitazone maleate in the pharmaceutical composition; and a desiccant, wherein the desiccant is sufficient to prevent the formation of more than 1.0% of the compound of formula (I) based on the combined weight of the compound of the formula (I) and rosiglitazone maleate in the pharmaceutical composition after storage of the sealed package for 3 months at 75% relative humidity and 40° C.

8. The sealed package of claim 7, wherein the compound of the formula (I):

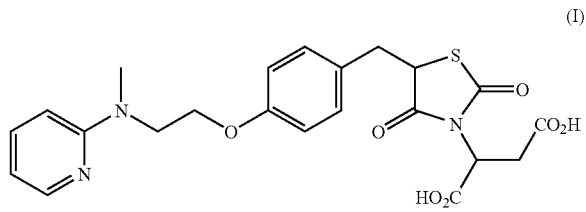

is present in the pharmaceutical composition in an amount of less than 0.1%, based on the combined weight of the compound of the formula (I) and rosiglitazone maleate.

9. The sealed package of claim 7, wherein a net increase of the total content of a compound of the formula (I):

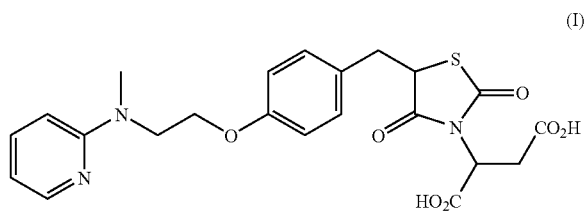

based on the combined weight of the compound of the formula (I) and rosiglitazone maleate in the pharmaceutical composition, is 0.7% or less after storage of the sealed package at 75% relative humidity and 40° C. for 3 months.

10. The sealed package of claim 7, wherein the pharmaceutical composition further comprises at least one disintegrant and at least one binder.

11. The sealed package of claim 10, wherein the disintegrant is croscarmellose sodium, and the binder is povidone.

12. The sealed package of claim 7, wherein the pharmaceutical composition further comprises a biguanide antidiabetic compound.

13. The sealed package of any of claim 12, wherein the biguanide antidiabetic compound is a pharmaceutically acceptable salt of metformin.

14. The sealed package of claim 13, wherein the pharmaceutically acceptable salt of metformin is metformin HCl.

15. The sealed package of claim 7, wherein the pharmaceutical composition further comprises a sulfonyl urea antidiabetic compound.

16. The sealed package of claim 15, wherein the sulfonyl urea antidiabetic compound is glimepride or glipizide.

17. The sealed package of claim 7, wherein the pharmaceutical composition is in the form of a tablet.

18. The sealed package of claim 17, wherein the tablet comprises a tablet core, the tablet core comprising, by weight, between 1% and 4% rosiglitazone maleate, 6% croscarmellose sodium, 2% povidone, between 0.5% and 1% magnesium stearate and between 87% and 90% filler, the filler consisting of lactose and microcrystalline cellulose.

19. The sealed package of claim 17, wherein the tablet comprises a tablet core, the tablet core comprising, by weight, between 75% and 76% metformin HCl, between 0.2% and 1% rosiglitazone maleate, between 5% and 6% povidone, between 1% and 2% croscarmellose sodium, between 4% and 5% starch, and between 0.5% and 1% magnesium stearate.

20. A process for preparing a pharmaceutical composition comprising rosiglitazone maleate and a pharmaceutically acceptable carrier, wherein in the pharmaceutical composition 2-N-{5-[[4-[2-(methyl-2-pyridinylamino)ethoxy]phenyl]methyl]-2,4-thiazolidinedione}-butanedioic acid is present in an amount of less that 1.2%, based on the combined weight of 2-N-{5-[[4-[2-(methyl-2-pyridinylamino)ethoxy]phenyl]methyl]-2,4-thiazolidinedione}-butanedioic acid and rosiglitazone maleate, comprising:

a) obtaining rosiglitazone maleate drug substance;

b) determining the total amount of 2-N-{5-[[4-[2-(methyl-2-pyridinylamino)ethoxy]phenyl]methyl]-2,4-thiazolidinedione}-butanedioic acid present in the rosiglitazone maleate drug substance; and c) including the rosiglitazone maleate drug substance in the preparation of the pharmaceutical composition only if the drug substance is determined to have less than 0.10% by weight of 2-N-{5-[[4-[2-(methyl-2-pyridinylamino)ethoxy]phenyl]methyl]-2,4-thiazolidinedione}-butanedioic acid.

* * * * *